(12) United States Patent
Barra et al.

(10) Patent No.: US 9,056,055 B2
(45) Date of Patent: Jun. 16, 2015

(54) FLAVOURED CLAY-BASED THERAPEUTIC COMPOSITION

(71) Applicants: Ipsen Pharma S.A.S., Boulogne-Billancourt (FR); Firmenich S.A., Geneva 8 (CH)

(72) Inventors: Jérôme Barra, Verrieres (FR); Denis Le Hazif, Vernouillet (FR)

(73) Assignees: IPSEN PHARMA S.A.S., Boulogne-Billancourt (FR); FIRMENICH S.A., Geneva (CH)

( * ) Notice: Subject to any disclaimer, the term of this patent is extended or adjusted under 35 U.S.C. 154(b) by 0 days.

(21) Appl. No.: 14/178,445

(22) Filed: Feb. 12, 2014

(65) Prior Publication Data

US 2014/0377354 A1 Dec. 25, 2014

Related U.S. Application Data

(63) Continuation of application No. 12/733,172, filed as application No. PCT/FR2008/001185 on Aug. 12, 2008, now abandoned.

(30) Foreign Application Priority Data

Aug. 13, 2008 (EP) ...................... 0729100

(51) Int. Cl.
| | | |
|---|---|---|
| A61K 9/48 | (2006.01) |
| A61K 33/12 | (2006.01) |
| A61K 9/00 | (2006.01) |
| A61K 33/06 | (2006.01) |
| A61K 35/02 | (2006.01) |

(52) U.S. Cl.
CPC ............. *A61K 9/4816* (2013.01); *A61K 9/0056* (2013.01); *A61K 9/0095* (2013.01); *A61K 33/06* (2013.01); *A61K 35/02* (2013.01); *A61K 33/12* (2013.01)

(58) Field of Classification Search
USPC .......................................... 514/642
See application file for complete search history.

(56) References Cited

U.S. PATENT DOCUMENTS

| | | |
|---|---|---|
| 4,610,890 A | 9/1986 | Miller et al. |
| 4,707,367 A | 11/1987 | Miller et al. |
| 6,187,351 B1 | 2/2001 | Porzio et al. |

FOREIGN PATENT DOCUMENTS

| | | |
|---|---|---|
| EP | 0 919 239 | 6/1999 |
| JP | 61 194014 | 8/1986 |
| KR | 2003 0050 958 | 6/2003 |
| WO | WO 2007/051427 | 5/2007 |
| WO | WO 2007/132095 | 11/2007 |

OTHER PUBLICATIONS

Database WPI Week 200377, Thomson Scientific, London, GB, XP002469755 (2003).
Database WPI Week 200377 Thomson Scientific, London, GB, XP002469756 (2007).
Database WPI Week 200377 Thomson Scientific, London, GB, XP002469757 (1986).
International Search Report for International Application No. PCT/FR2008/001185, mailed Mar. 10, 2009.
Li, Chunwen & Zhao, Qiong; "Applications of Domestic Smectite Powder, "Bigi", and Imported Smectite Powder, "Smecta", to Diarrhea;" Dec. 9, 2001, 2 pages (Chinese); 4 pages (English).
Formulation Néosmectine commercialisée par Farmproekt, (2005), ZAO, Russie, 3 pgs.
Smecta, powder for oral suspension, 2007, http://home.intek.com/pharm/pharmpln/smecta.html, pp. 1-2.
Smecta 3GM Medical Services Kuang Tien General Hospital (3 pages).

*Primary Examiner* — Walter Webb
(74) *Attorney, Agent, or Firm* — Hunton & Williams LLP

(57) ABSTRACT

The subject of the present invention is a flavored therapeutic composition containing a clay as the active principle, and characterized in that the clay is a dioctahedral smectite and the flavor is encapsulated.

24 Claims, No Drawings

FLAVOURED CLAY-BASED THERAPEUTIC COMPOSITION

The present Application relates to a flavoured pharmaceutical composition containing a smectite as active ingredient.

A therapeutic composition based on smectite known as "diosmectite" exists and is sold under the trade-mark Smecta®. But due to the particular taste of the clay which certain patients and children in particular can sometimes find unpleasant, the problem was therefore to find a novel composition which is flavoured and the taste of which remains predominant vis-à-vis the taste of the clay. In order to solve this problem, the Applicant proposes a novel flavoured pharmaceutical composition based on smectite and as defined below.

The subject of the present invention is therefore a flavoured therapeutic composition containing a clay as active ingredient, and characterized in that the clay is a dioctahedral smectite; and
the flavour is encapsulated.

A composition according to the present invention can be used for the prevention and/or treatment of certain pathologies such as the symptomatic treatment of pain associated with oesogastroduodenal and colic conditions, acute and chronic diarrhoeas, coeliac disease.

Smectites represent a particular family of clay in which dioctaedral species such as montmorillonite and beidellite, and trioctaedral species such as hectorite and saponite are found.

The clay used according to the invention is a dioctahedral smectite. Preferably, the dioctahedral smectite is a montmorillonite or a beidellite or a crystallographic structure intermediate between the two crystal-chemical poles: montmorillonite and beidellite. This intermediate crystallographic structure can be close to the montmorillonite pole and even very close to the montmorillonite pole; it can also be close to the beidellite pole and even very close to the beidellite pole. Preferably, a smectite according to the invention is a montmorillonite or an intermediate structure close to the montmorillonite pole, and very preferably very close to the montmorillonite pole.

Also preferably, the clay used is the smectite known as "diosmectite" and sold under the trade-mark Smecta®.

The therapeutic composition according to the present invention comprises "a flavouring ingredient or composition", called "flavour". The term "flavour" as used in the present Application covers the flavouring ingredients or compositions usually used in the food industry, whether of natural or synthetic origin. It comprises single compounds or mixtures.

Specific examples of such compounds can be found in the literature, such as for example in Fenaroli's Handbook of Flavor Ingredients, 1975, CRC Press; Synthetic Food Adjuncts, 1947, M. B. Jacobs, published by Van Nostrand; or Perfume and Flavor Chemicals, 1969, S. Arctander, Montclair, N.J. (USA).

These compounds are well known to a person skilled in the art in the field of flavouring or aromatizing consumer products, i.e. traditionally flavoured consumer products to which an odour, a flavour or a taste has been added, or consumer products the taste of which has been modified.

Preferably, the flavour is a hydrophobic liquid, soluble in organic solvents but only very weakly soluble in water.

Very preferably, the flavour is characterized by a Hildebrand solubility parameter $\delta$ less than 30 MPa$^{1/2}$. The incompatibility with water of most of the flavours and perfumes can in fact be expressed by means of the Hildebrand solubility parameter which is in general less than 25 MPa$^{1/2}$ while the same parameter for water is 48 MPa$^{1/2}$ and for alkanes, 15-16 MPa$^{1/2}$. This parameter gives a useful polarity scale correlated with a cohesive energy density of the molecules. For mixing to take place spontaneously, the difference in solubility of the molecules to be mixed must be kept to a minimum. The handbook of solubility parameters (Handbook of Solubility Parameters, A. F. M. Barton, CRC Press, Bocca Raton, 1991) gives a list of $\delta$ values for a large number of chemical products but also recommended group-contribution methods allowing the $\delta$ values for complex chemical structures to be calculated.

Also preferably, the flavour is in a liquid, volatile or labile form, with a log P comprised within the range −2 to 7, and very preferably, from 2 to 6.

Also in a preferred fashion, a composition according to the present invention comprises, as flavour, natural extracts, essential oils or a mixture thereof.

As a suitable flavour, traditional flavours can be mentioned such as liquorice, exotic fruits, red fruits, extracts of citrus fruits such as lime, lemon, orange, grapefruit, or mandarin oils or coffee, tea, mint, cocoa, vanilla/caramel or essential oils from herbs and spices, or also flavours known as "modern" such as coca-cola, green tea, caramel custard.

Preferably, a composition according to the invention comprises at least one encapsulated flavour different from vanilla.

The flavours are preferably chosen from the traditional flavours such as liquorice, exotic fruits, red fruits, extracts of citrus fruits, vanilla/caramel/chocolate but also flavours known as "modern" such coca-cola, green tea, caramel custard.

Preferably, the flavour is chosen from vanilla/caramel/chocolate flavours and extracts of citrus fruits and very preferably, vanilla/caramel/chocolate and orange, lemon, grapefruit or clementine.

Also in a preferred fashion, the flavour is a mixture of flavours, and very preferably, a mixture of vanilla and orange flavours.

The flavour can be mixed with solvents, adjuvants, additives and/or other substances, for example those usually used in the flavour and/or food industry.

The flavour according to the present invention is preferably encapsulated in a glassy matrix (encapsulation matrix) of carbohydrate(s).

Any sugar or sugar derivative which can be processed by extrusion techniques can be used as constituent(s) of the encapsulation matrix, in order to form a dry extruded solid. Particular examples of suitable constituents can be chosen from the following products: sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysates, maltodextrin, Stabilite (trade name; origin: SPI Polyols, USA), agar, carrageenan, other gums, polydextrose and the derivatives and mixtures thereof.

Preferably, maltodextrin or mixtures of maltodextrin and at least one product chosen from: sucrose, glucose, lactose, levulose, maltose, fructose, isomalt, sorbitol, mannitol, xylitol, lactitol, maltitol and hydrogenated starch hydrolysates are used. Very preferably, the matrix is constituted by maltodextrin or a mixture of maltodextrin and at least one product chosen from: sucrose, maltose, isomalt, maltitol and hydrogenated starch hydrolysates. Also very preferably, the matrix is constituted by maltodextrin and sucrose.

Preferably, the maltodextrin has a dextrose equivalent (DE) greater than 5 and less than 20.

An emulsifier such as lecithin, and/or a plasticizer, typically water, can be added to the mixture if necessary.

The flavoured product or the flavoured composition according to the invention, which are extruded, can be prepared by any standard method. For example, the methods described in U.S. Pat. Nos. 4,610,890 and 4,707,367, the content of which is incorporated by way of reference, are suitable for supplying encapsulated flavours as used in the present invention.

Also preferably, the flavour is present in a proportion of at least 10% by weight expressed as dry matter, with respect to the total weight (expressed as dry matter) of the encapsulation matrix, and preferably in a proportion comprised between 15 and 35%.

A composition according to the invention comprises preferably 70 to 90% by weight of active ingredient, and very preferably from 75 to 85%, with respect to the total weight of the composition.

Also preferably, a composition according to the invention comprises 0.1 to 3% by weight of encapsulated flavour with respect to the total weight of the composition, and very preferably 0.3 to 2.5%. Also very preferably, a composition according to the invention comprises 0.5 to 2% by weight of encapsulated flavour with respect to the total weight of the composition.

A therapeutic composition according to the present invention can be presented in different solid forms such as for example powders, granules, tablets or capsules. Appropriate solid supports can be, for example, talc, sugars, lactose, dextrin, gelatin, cellulose and its esters.

In a therapeutic composition according to the present invention, there can also be also other additives such as colouring agents, sweetening agents, lubricants, glidants. A composition according to the present invention can also contain minerals.

The colouring agent(s) used according to the present invention can be any type of colouring agents usually used in the food and/or the pharmaceutical industries. Among the sweetening agents, the following can be mentioned: saccharin, aspartame, maltodextrin, monosaccharides such as fructose or glucose, disaccharides such as saccharose. Among the lubricating agents, talc can be mentioned for example. Among the glidant agents, saccharose can be mentioned.

The mineral contribution can for example consist of the addition of metal salts such as aluminium or magnesium salts such as aluminium hydroxide, magnesium carbonate.

The administration method for a composition according to the invention is chosen, among others, according to its pharmaceutical form and the pathology to be treated. Preferably, the composition as defined above is administered by the oral route.

The daily administration dose is the usual recommended dose for this product. In the particular case of the smectite known as "diosmectite", it can be administered at a maximum daily dose of 18 g/day.

Unless defined otherwise, all the technical and scientific terms used here have the same meaning as that usually understood by an ordinary specialist in the field to which this invention belongs.

EXPERIMENTAL PART

Example 1

Preparation of an Encapsulated Orange (Oil) Flavour

A syrup is prepared from maltodextrin, sucrose, water and flavour. The mixture is then heated to 123° C. in order to reduce the moisture content of the syrup. Then, the emulsifier is mixed with the concentrated syrup under high shear conditions in order to form a uniform melt. The melt is then extruded under a pressure of $2\times10^5$ Pa through an extrusion die plate with holes of 0.8 mm diameter in a cold solvent for chilling and breaking of the extrudates.

| Ingredients | in grams (g) | % dry matter |
|---|---|---|
| Maltodextrin 18DE | 1505 | 44.55 |
| Sucrose | 1505 | 44.55 |
| Cold-pressed oil of Valencia orange | 350 | 10.36 |
| Soya lecithin[1)] | 18 | 0.54 |
| Water | 400 | — |
| Total | | 100.00 |

[1)]origin: Central Soya, Strong Wayne, Indiana, USA

Example 2

Preparation of an Encapsulated Vanilla Flavour

Example 1 is reproduced by using a vanilla extract (ex Firmenich) instead of the orange flavour.

Example 3

Preparation of an Encapsulated Caramel Flavour

Example 1 is reproduced by using a caramel flavour (ex Firmenich) instead of the orange flavour.

Example 4

Preparation of a Flavoured Therapeutic Composition

The compositions below are prepared by gently mixing all the substances together in the proportions indicated, until they are dispersed in a homogenous fashion. In the table below, all the quantities are expressed in mg.

| Ingredients | Example 4a | Example 4b | Example 4c |
|---|---|---|---|
| Diosmectite | 3000 | 3000 | 3000 |
| Encapsulated orange flavour (flavour prepared according to Example 1)[1] | — | — | 10 |
| Encapsulated vanilla flavour (flavour prepared according to Example 2)[2] | 50 | 50 | 50 |
| Encapsulated caramel ® flavour (flavour prepared according to Example 3)[3] | 10 | — | — |
| Soluble saccharine + hydrated glucose | 700 | 710 | 700 |
| Water | 100 | 100 | 100 |

[1]ex Firmenich, ref. 501289 TD 0990B;
[2]ex Firmenich, ref. 501465 TD1591;
[3]ex Firmenich, ref. 501403 TD 1094

Example 5

Stability of a Composition According to the Invention

Clay being a stable product naturally, the stability of a composition according to the invention is measured both as regards the organoleptic characteristics of the flavour and for its inertia vis-à-vis the clay.

The stability of the organoleptic characteristics of the flavour is established by testers (panel of 7 experts) on the basis of a number of criteria (sugary, fruity, acidic, bitterness, etc.) over a period of at least 6 months.

Moreover, it is noted that the flavour shows no deterioration in the presence of the clay over this same period.

The invention claimed is:

1. A composition comprising 70 to 90% by weight a dioctahedral smectite clay and a flavor encapsulated in a glassy matrix of carbohydrates.

2. The composition of claim 1, wherein the dioctahedral smectite is a montmorillonite or a beidellite or an intermediate crystallographic structure between the montmorillonite and beidellite crystal-chemical poles.

3. The composition of claim 2, wherein the dioctahedral smectite is a montmorillonite or an intermediate crystallographic structure close to the montmorillonite pole.

4. The composition of claim 1, wherein the dioctahedral smectite is diosmectite.

5. The composition of claim 1, wherein the flavor is a hydrophobic liquid.

6. The composition of claim 1, wherein the flavor has a Hildebrand solubility parameter less than 30 $MPa^{1/2}$.

7. The composition of claim 1, wherein the flavor is in liquid form with a log P comprised within the range −2 to 7.

8. The composition of claim 1, wherein the composition at least one encapsulated flavor is a natural extract, an essential oil, or a mixture thereof.

9. The composition of claim 1, wherein the flavor is different from vanilla.

10. The composition of claim 1, wherein the flavor is liquorice, exotic fruits, red fruits, extracts of citrus fruits, vanilla, caramel, chocolate, coca-cola, green tea, caramel custard, or a mixture thereof.

11. The composition of claim 1, wherein the the flavor is vanilla, caramel, chocolate, extracts of citrus fruits, or a mixture thereof.

12. The composition of claim 1, wherein the flavor is vanilla, caramel, chocolate, orange, lemon, grapefruit, clementine, or a mixture thereof.

13. The composition of claim 1, wherein the flavor is a mixture of flavors.

14. The composition of claim 13, wherein the flavor is a mixture of vanilla and orange flavors.

15. The composition of claim 1, wherein the matrix is constituted by maltodextrin or a mixture of maltodextrin and at least one of sucrose, glucose, lactose, levulose, maltose, fructose, isomalt, sorbitol, mannitol, xylitol, lactitol, maltitol, hydrogenated starch hydrolysates, or mixtures thereof.

16. The composition of claim 15, wherein the matrix is constituted by maltodextrin or a mixture of maltodextrin and at least one of sucrose, maltose, isomalt, maltitol, hydrogenated starch hydrolysate, or mixtures thereof.

17. The composition of claim 16, wherein the matrix is constituted by maltodextrin and sucrose.

18. The composition of claim 17, wherein the maltodextrin has a dextrose equivalent greater than 5 and less than 20.

19. The composition of claim 1, wherein the flavour is present in a proportion of at least 10% by weight expressed as dry matter, with respect to the total weight expressed as dry matter of the encapsulation matrix.

20. The composition of claim 1, wherein the flavour is present in a proportion comprised between 15 and 35% by weight expressed as dry matter, with respect to the total weight expressed as dry matter of the encapsulation matrix.

21. The composition of claim 1, wherein said clay comprises from 75 to 85% by weight of said composition.

22. The composition of claim 1, wherein said clay comprises from 0.1 to 3% by weight of encapsulated flavour.

23. The composition of claim 22, wherein said clay comprises from 0.3 to 2.5% by weight of encapsulated flavour.

24. The composition of claim 23, wherein said clay comprises from 0.5 to 2% by weight of encapsulated flavour.

* * * * *